(12) United States Patent  (10) Patent No.: US 12,224,057 B2
Zhang et al.  (45) Date of Patent: Feb. 11, 2025

(54) MEDICAL IMAGE PROCESSING METHOD, PROCESSING APPARATUS, AND COMPUTER-READABLE STORAGE MEDIUM

(71) Applicant: SHENZHEN INSTITUTES OF ADVANCED TECHNOLOGY, Shenzhen (CN)

(72) Inventors: Na Zhang, Shenzhen (CN); Hairong Zheng, Shenzhen (CN); Xin Liu, Shenzhen (CN); Zhanli Hu, Shenzhen (CN); Zhiyuan Huang, Shenzhen (CN); Dong Liang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 360 days.

(21) Appl. No.: 17/739,121

(22) Filed: May 8, 2022

(65) Prior Publication Data
US 2022/0262498 A1  Aug. 18, 2022

Related U.S. Application Data

(63) Continuation of application No. PCT/CN2020/103371, filed on Jul. 21, 2020.

(51) Int. Cl.
*G16H 30/00* (2018.01)
*G06N 3/084* (2023.01)
(Continued)

(52) U.S. Cl.
CPC ............ *G16H 30/40* (2018.01); *G06N 3/084* (2013.01); *G06T 5/70* (2024.01); *G06V 10/751* (2022.01); *G06V 10/7753* (2022.01)

(58) Field of Classification Search
CPC .. G16H 30/40; G06V 10/751; G06V 10/7753; G06T 5/70; G06N 3/084
See application file for complete search history.

(56) References Cited

U.S. PATENT DOCUMENTS

| 2008/0310695 A1* | 12/2008 | Garnier | G06T 5/50 |
| | | | 382/131 |
| 2017/0091908 A1 | 3/2017 | Takeda et al. | |
| 2017/0178341 A1 | 6/2017 | El-Sheimy et al. | |

FOREIGN PATENT DOCUMENTS

| CN | 102203826 A * | 9/2011 | ............ G06T 5/002 |
| CN | 103927737 A | 7/2014 | |

(Continued)

OTHER PUBLICATIONS

Chinese First Office Action, Chinese Application No. 202010706526.7, mailed Nov. 30, 2023 (12 pages).

(Continued)

*Primary Examiner* — Khai M Nguyen

(57) ABSTRACT

A medical image processing method and processing apparatus, and a computer readable storage medium. The method includes: obtaining a to-be-processed image; performing a feature extraction on the to-be-processed image to obtain a corresponding feature image; and re-determining a pixel value of each pixel in the to-be-processed image based on first information and second information of a corresponding pixel in the feature image, and processing the to-be-processed image; wherein the first information is information of a pixel adjacent to the corresponding pixel in the features image, and the second information is information of a pixel that is not adjacent to and is similar to the corresponding pixel in the features image.

17 Claims, 2 Drawing Sheets

(51) Int. Cl.
  *G06T 5/70*  (2024.01)
  *G06V 10/75*  (2022.01)
  *G06V 10/774*  (2022.01)
  *G16H 30/40*  (2018.01)

(56) References Cited

FOREIGN PATENT DOCUMENTS

| CN | 107292897 | A | | 10/2017 | | |
|---|---|---|---|---|---|---|
| CN | 108259707 | A | | 7/2018 | | |
| CN | 109461495 | A | | 3/2019 | | |
| CN | 111340739 | A | | 6/2020 | | |
| CN | 111429370 | A | | 7/2020 | | |
| CN | 112836694 | A | * | 5/2021 | | |
| CN | 111582027 | B | * | 3/2024 | ............. | G06F 18/22 |

OTHER PUBLICATIONS

International search report and Written Opinion of the International Search Authority, International Application No. PCT/CN2020/103371, mailed Mar. 25, 2021 (12 pages).

Low-Dose CT with a Residual Encoder-Decoder Convolutional Neural Network (RED-CNN).

Generative Adversarial Networks for Noise Reduction in Low-Dose CT.

* cited by examiner

MEDICAL IMAGE PROCESSING METHOD, PROCESSING APPARATUS, AND COMPUTER-READABLE STORAGE MEDIUM

CROSS REFERENCE

The present application is a continuation-application of International (PCT) Patent Application No. PCT/CN2020/103371, filed on Jul. 21, 2020, the entire contents of which are hereby incorporated by reference in its entirety.

TECHNICAL FIELD

The present disclosure relates to the field of image processing technologies, and in particular to a medical image processing method, a processing apparatus, and a computer-readable storage medium.

BACKGROUND

Magnetic resonance imaging (MRI) is an examination method that converts a signal generated by radio frequency electromagnetic waves and hydrogen protons in the human body into an image after processing. The MRI technology has the advantages of safety without radiation, high soft tissue contrast, having many functional imaging methods, etc. The MRI technology is one of the most powerful and complex technologies in medical imaging technology at present. However, compared with other imaging modalities, the MRI technology has a disadvantage of slower data obtaining speed (longer scan time). For example, it is easy to cause low image resolution and motion artifacts during dynamic imaging, which restricts the wide application of the MRI technology in clinical practice. If the MRI scan time is shortened, an MR reconstruction image may have artifacts due to the insufficient amount of obtained data. Therefore, research and development of post-processing technology for MR image denoising has important scientific significance and broad application prospects for the current medical diagnosis field.

SUMMARY OF THE DISCLOSURE

The present disclosure provides a medical image processing method, comprising: obtaining a to-be-processed image; performing a feature extraction on the to-be-processed image to obtain a corresponding feature image; and re-determining a pixel value of each pixel in the to-be-processed image based on first information and second information of a corresponding pixel in the feature image, and processing the to-be-processed image; wherein the first information is information of a pixel adjacent to the corresponding pixel in the features image, and the second information is information of a pixel that is not adjacent to and is similar to the corresponding pixel in the features image.

The present disclosure further provides a medical image processing apparatus, comprising a memory, a processor, and a computer program stored in the memory and executable by the processor; wherein the processor is capable of executing the computer program to implement the medical image processing method as described above.

The present disclosure further provides a non-transitory computer-readable storage medium, storing a computer program; wherein the computer program is executable by a processor to implement the medical image processing method as described above.

BRIEF DESCRIPTION OF THE DRAWINGS

In order to more clearly illustrate the embodiments of the present disclosure or the technical solutions in the prior art, the following briefly introduces the accompanying drawings required for the description of the embodiments or the prior art. Obviously, the drawings in the following description are only some embodiments of the present disclosure. For those skilled in the art, other drawings can also be obtained from these drawings without creative work.

DETAILED DESCRIPTION

The technical solutions in the embodiments of the present disclosure will be clearly and completely described below with reference to the drawings in the embodiments of the present disclosure. Obviously, the described embodiments are only a part of the embodiments of the present disclosure, but not all of the embodiments. Based on the embodiments in the present disclosure, all other embodiments obtained by those skilled in the art without creative efforts shall fall within the scope of the present disclosure.

It should be understood that although the terms "first", "second", "third", etc. may be used in the present disclosure to describe various information, such information should not be limited by these terms. These terms are only intended to distinguish the same type of information from other. For example, first information may also be referred to as second information, and similarly, the second information may also be referred to as the first information without departing from the scope of the present disclosure. Depending on the context, the term "if" as used herein may be interpreted as "in condition of" or "when", or "in response to".

Figure 1:
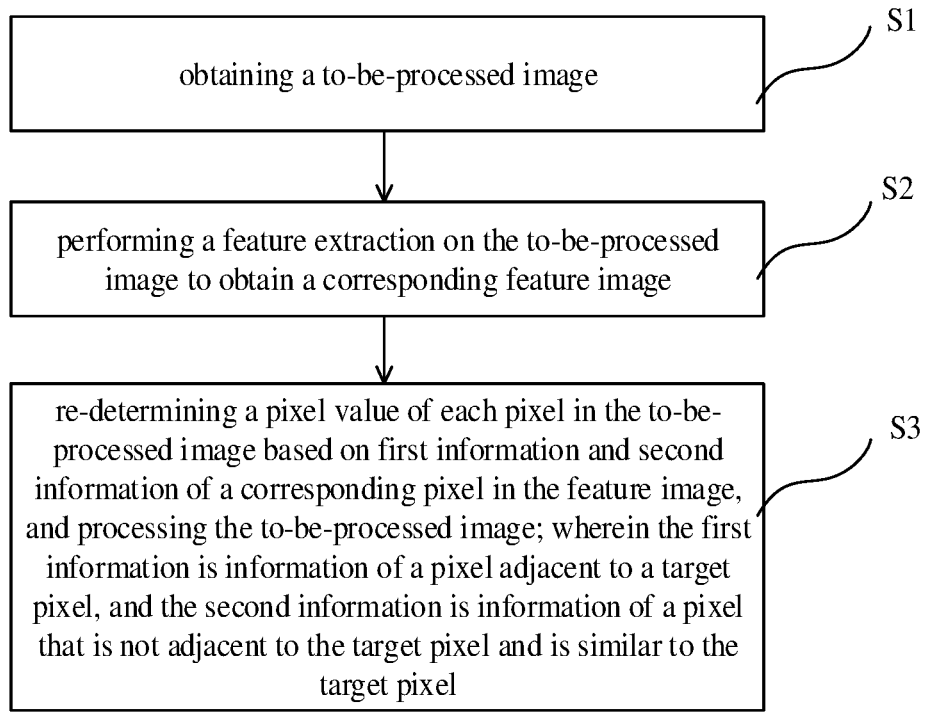
FIG. 1 is a flowchart of a medical image processing method according to an embodiment of the present disclosure.

Referring to FIG. 1, FIG. 1 is a flowchart of a medical image processing method according to an embodiment of the present disclosure. The medical image processing method may include operations at blocks illustrated herein.

At block S1: obtaining a to-be-processed image.

Specifically, the to-be-processed image in the embodiments may be a common medical image, such as a magnetic resonance image, a computed tomography (CT) image, an X-ray image, a B-scan ultrasonography image, etc., and may be, for example, a magnetic resonance image of a human brain. However, it is to be noted that the above magnetic resonance image of the human brain is only an exemplary description, and in actual implementation, the to-be-processed image may be a medical image of other parts of a target, which is not limited in the present disclosure.

At block S2: performing a feature extraction on the to-be-processed image to obtain a corresponding feature image.

In some embodiments, the feature extraction on the to-be-processed image may be performed in a convolution manner. Specifically, a plurality of convolution kernels of different sizes are used to convolve the to-be-processed image, so as to output a multi-channel feature image of the to-be-processed image. For example, when the to-be-processed image is input into a convolution layer containing convolution kernels of 3×3, 5×5, and 7×7 sizes, a feature image with the number of channels of 3 is output, and each pixel of the feature image includes a three-dimensional feature vector.

At block S3: re-determining a pixel value of each pixel in the to-be-processed image based on first information and second information of a corresponding pixel in the feature image, and processing the to-be-processed image; wherein the first information is information of a pixel adjacent to a target pixel, and the second information is information of a pixel that is not adjacent to the target pixel and is similar to the target pixel.

It is found that most of the denoising methods for medical images in the prior art only use information of a pixel, in the image, that is adjacent to a target pixel to denoise the image, such as bilinear filtering method and median filtering method. However, information of a pixel that is not adjacent to the target pixel but similar to the target pixel is not considered. Although the pixel corresponding to the said information is far away from the target pixel in terms of spatial distance, a certain number of these pixels exist that are similar to the target pixel due to large amount of information redundancy that generally exists in the image. Therefore, in the present disclosure, during the denoising process of the to-be-processed image, the first information in the image (i.e., the information of a pixel adjacent to the target pixel) and the second information (i.e., the information of a pixel that is non-adjacent but similar to the target pixel) are combined to denoise the image, such that the denoised image is clearer, thereby improving the image quality.

Specifically, the operation S3 may be implemented through the following sub-operations:

S31: obtaining pixels in a neighborhood with a radius r around the target pixel in the feature image to form a first pixel set, and obtaining pixels similar to the target pixel and located outside the neighborhood to form a second pixel set; wherein r is a preset neighborhood radius parameter, being a positive integer. For example, assuming that r is equal to 1, surrounding 8 pixels with the target pixel as the center are taken as first pixels constituting the first pixel set. A Euclidean distance between a feature vector of the target pixel and a feature vector of each pixel outside the neighborhood of radius r is calculated, and N pixels with the smallest Euclidean distance are obtained to form the second pixel set. In the second pixel set, the less the Euclidean distance, the greater a second contribution rate of the corresponding second pixel. N is a positive integer. Specifically, assuming that the feature image corresponding to the to-be-processed image of size L×H×W is $H^l \in R^{C \times H \times W}$, and the feature vector of any pixel i in the feature space $H^l$ is $H^l_i \in R^{C \times 1}$, then the Euclidean distance between pixel i and pixel j in the feature space is:

$$d^l(i, j) = |H^l_i - H^l_j|$$

The above formula is applied to calculate the Euclidean distance between each pixel outside the neighborhood in the feature space and the target pixel, and the N pixels with the smallest Euclidean distance are taken to form the second pixel set $N^l_i$.

S32: obtaining a first contribution rate of each first pixel in the first pixel set to the target pixel, and obtaining a second contribution rate of each second pixel in the second pixel set to the target pixel; wherein a sum of all the first contribution rates and all the second contribution rates is 1.

In this sub-operation, effective information may be obtained from the first information and the second information. That is, the first pixel and the second pixel obtained in sub-operation S32 are given weighted values. For example, the more similar the second pixel is to the target pixel, the higher the corresponding second contribution rate.

S33: for each first pixel, multiplying a pixel value and the corresponding first contribution rate of the first pixel to obtain a first product; for each second pixel, multiplying a pixel value and the corresponding second contribution rate of the second pixel to obtain a second product; and adding all the first products with all the second products to obtain a sum, and taking the sum as a pixel value of the target pixel.

Specifically, after obtaining the first pixel adjacent to the target pixel and the second pixel that is not adjacent but similar to the target pixel, the pixel value of the target pixel may be re-determined based on the above two types of pixels. For example, the pixel values of all the first pixels and the second pixels may be averaged as the pixel value of the target pixel; that is, all the first contribution rates and the second contribution rates are equal. However, in order to make the obtained pixel value of the target pixel more accurate, in some embodiments, the first contribution rate and the second contribution rate may be obtained by presetting a convolutional neural network M.

In the medical image processing method provided in the embodiments, a to-be-processed image is subjected to a feature extraction to obtain a corresponding feature image; and for each pixel in the feature image, information of a pixel adjacent to the pixel in the feature image and information of a pixel non-adjacent but similar to the pixel in the feature image is applied to re-determine the pixel value of the pixel in the to-be-processed image, thereby solving problems in the prior art that the quality of the obtained image is poor due to loss of detail information caused by only using information of pixels adjacent to each pixel to denoise the image.

Figure 2:
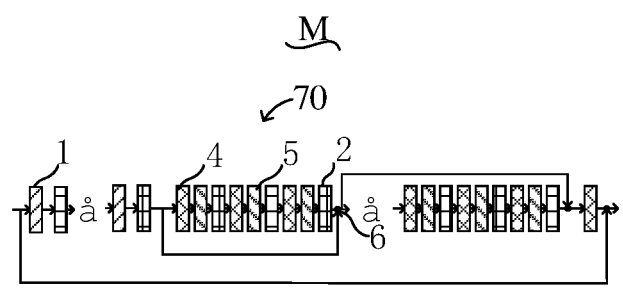
FIG. 2 is a structural schematic view of a convolutional neural network according to an embodiment of the present disclosure.

Referring to FIG. 2, FIG. 2 is a structural schematic view of a convolutional neural network according to an embodiment of the present disclosure. In order to realize the above processing method for medical images, a preset convolutional neural network M is established in the embodiments, and the preset convolutional neural network M includes at least one feature extraction layer 1, at least one denoising layer 4, at least one batch of normalization layers 5, and at least one activation layer 2. Among them, each feature extraction layer 1 is connected to an activation layer 2, and each denoising layer 4 is sequentially connected to a batch of normalization layers 5 and an activation layer 2.

In some embodiments, the preset convolutional neural network M may further include at least one adaptive residual unit 70 connected in series. Each adaptive residual unit 70 includes three denoising layers 4, three activation layers 2, three batches of normalization layers 5, and one adaptive skip connection unit 6. Therefore, the preset convolutional neural network M includes K+1 adaptive skip connection units 6, where K represents the number of adaptive residual units 70 included in the preset convolutional neural network M.

Specifically, an input and an output are directly connected through the adaptive skip connection unit 6 to reserve more detailed information of the input image, enhancing the feature extraction on the preset convolutional neural network M and increasing the convergence speed of the training process of the preset convolutional neural network M, thereby greatly enhancing the learning ability of the preset convolutional neural network M. For example, the adaptive skip connection unit 6 in the embodiments may connect the input and output directly through unit mapping.

Figure 3:
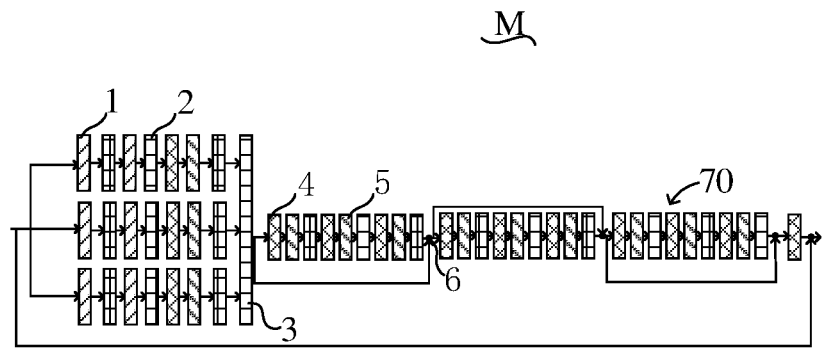
FIG. 3 is a structural schematic view of a convolutional neural network according to another embodiment of the present disclosure.

Referring to FIG. 3, FIG. 3 is a structural schematic view of a convolutional neural network according to another embodiment of the present disclosure. The preset convolutional neural network M may include six feature extraction layers 1, thirteen denoising layers 4, eighteen activation layers 2, twelve batches of normalization layers 5, a fusion layer 3, and four adaptive skip connection units 6. The preset convolutional neural network M further includes three adaptive residual units 70 connected in series, and each adaptive residual unit 70 includes three denoising layers 4, three activation layers 2, three batches of normalization layers 5, and an adaptive skip connection unit 6.

The feature extraction layer 1 is configured to receive a to-be-processed image and perform a feature extraction on the to-be-processed image to obtain a corresponding feature image. The fusion layer 3 is configured to fuse images output by the activation layers 2 and input the images into the denoising layers 4. The denoising layers 4 are configured to re-determine a pixel value of each pixel in the to-be-processed image based on first information and second information of a corresponding pixel in the feature image, and processing the to-be-processed image; wherein the first information is information of a pixel adjacent to a target pixel, and the second information is information of a pixel that is not adjacent to the target pixel and is similar to the target pixel.

The introduction of the adaptive skip connection unit 6 directly connects the input and output, thereby reserving more detailed information of the input image, enhancing the feature extraction of the preset convolutional neural network M, and increasing the convergence speed of the training process of the preset convolutional neural network M.

Specifically, the denoising layers 4 are configured to re-determine the pixel value of each pixel in the to-be-processed image by using the first information and the second information of each pixel in the feature image, and then process the to-be-processed image. The first information is information of a pixel adjacent to a target pixel, and the second information is information of a pixel that is not adjacent to the target pixel and is similar to the target pixel. Specifically, the following formula may be used to express:

$$H_i^{l+1} = \sigma \left( \Sigma_{j \in N_i^l} \frac{F^l[d^l(i,j)] \cdot H_j^l}{|N_i^l|} + W^l \cdot H_i^l + b^l \right)$$

where $\sigma$ represents a nonlinear activation function, such as Sigmoid function, relu function, or Hanh function. $F^l[d^l(i,j)]$ represents the second contribution rate, and the second contribution rate is determined by the Euclidean distance $d^l(i,j)$ between the second pixel and the target pixel. $W^l$ represents the first contribution rate, $b^l$ represents a bias, $H_i^l$ represents the first pixel, $H_j^l$ represents the second pixel, and $H_i^{l+1}$ represents the denoised image.

After the preset convolutional neural network M is established, an unprocessed medical image and a corresponding processed medical image may be obtained as a training data set. The preset convolutional neural network M may be trained with the unprocessed medical image as input data and the corresponding processed medical image as a ground truth label.

Specifically, the unprocessed medical image is a medical image obtained under a scanning condition less than a set time period, and the corresponding processed medical image is a medical image obtained under a scanning condition greater than the set time period. The set time period may refer to a time period determined by multiple medical imaging experiments. When the scanning time is longer than the time period, the obtained medical image quality is good. When the scanning time is shorter than or equal to the time period, the obtained corresponding medical image quality may be observed poor.

The preset convolutional neural network M may be trained through a mean square error (MSE) loss function. The formula for calculating MSE is as follows:

$$J(\theta) = \frac{1}{m} \sum_{i=1}^{m} \frac{1}{2} (y^i - h_\theta(x^i))^2$$

where $J(\theta)$ is the mean square error loss function, m is the total number of input unprocessed medical image pixels, $h_\theta(x^i)$ is the pixel value of an ith pixel in the image output by the preset convolutional neural network M, and $x^i$ is the pixel value of the ith pixel in the input unprocessed image, and $y^i$ represents the pixel value of the ith pixel in the processed medical image corresponding to the unprocessed medical image.

The model parameter $\theta$ of the preset convolutional neural network M may be updated through a gradient back-propagation algorithm, such that the loss function tends to be minimized. Specifically, a gradient descent algorithm is required to be applied when the gradient back-propagation algorithm is performed to train the network parameter $\theta$ such as the first contribution rate and the second contribution rate. Commonly applied gradient descent algorithms include batch gradient descent, stochastic gradient descent, mini-batch gradient descent, etc. In the embodiments, the gradient descent algorithm used is stochastic gradient descent. Of course, other gradient descent algorithms may be used, depending on the specific situation, which is not specifically limited herein.

Specifically, in the training process of the preset convolutional neural network M, a partial derivative of the MSE function is obtained for the parameter $\theta$ required to be determined by training, and the gradient of the loss function is:

$$\frac{\partial J(\theta)}{\partial \theta_j} = -\frac{1}{m} \sum_{i=1}^{m} (y^i - h_\theta(x^i)) x_j^i$$

After obtaining the gradient of the loss function, the parameter $\theta$ in the convolutional layer may be updated by the following formula:

$$\theta_j = \theta_{j-\eta} \times \nabla_\theta J(\theta; x^{(i)}, y^{(j)})$$

In the preset convolutional neural network M provided by the present disclosure, the parameters $\theta$ required to be determined include the first contribution rate $W^l$, the second contribution rate $F^l[d^l(i,j)]$ of the denoising layer, the bias parameter $b^l$, and a preset weight parameter W and bias term b of other convolutional layers in the convolutional neural network M.

In the embodiments, the to-be-processed image is input into the preset convolutional neural network M, and the preset convolutional neural network M is configured to perform feature extraction on the to-be-processed image, so as to obtain the corresponding feature image and to redetermine the pixel value of each pixel in the to-be-processed image using the first information and the second information of corresponding each pixel in the feature image, thereby processing the to-be-processed image. In addition, through the training of the preset convolutional neural network M, optimal model parameters may be obtained, thereby improving the effective processing of information by the network, and further improving the quality of the output image.

Figure 4:
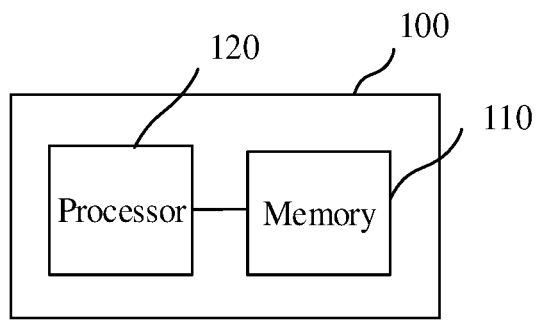
FIG. 4 is a structural schematic view of a medical image processing apparatus according to an embodiment of the present disclosure.

Referring to FIG. 4, FIG. 4 is a structural schematic view of a medical image processing apparatus according to an embodiment of the present disclosure. A processing apparatus 100 includes a memory 110 and a processor 120. The memory 110 is configured to store a computer program, and the processor 120 is configured to execute the computer program to implement the operations of the medical image processing method provided by the present disclosure. The processor 120 may be a central processing unit (CPU), or an application specific integrated circuit (ASIC), or one or more integrated circuits configured to implement the embodiments of the present disclosure.

The memory 110 is configured to store executable instructions. The memory 110 may include a high-speed RAM memory 110, and may also include a non-volatile memory 110, such as at least one disk memory. Memory 110 may also be a memory array. The storage 110 may also be divided into blocks, and the blocks may be combined into virtual volumes according to a certain rule. The instructions stored in the memory 110 may be executed by the processor 120 to enable the processor 120 to perform the medical image processing method in any of the above embodiments.

Figure 5:
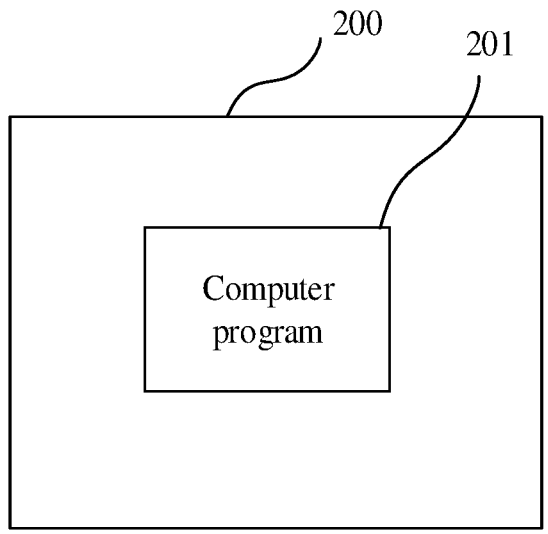
FIG. 5 is a structural schematic view of a computer-readable storage medium according to an embodiment of the present disclosure.

Referring to FIG. 5, FIG. 5 is a structural schematic view of a computer-readable storage medium according to an embodiment of the present disclosure. A computer program 201 is stored in a computer-readable storage medium 200. When the computer program 201 is executed by a processor, the operations of the medical image processing method provided in the present disclosure are implemented. The computer storage medium 200 may be any available medium or data storage device that can be accessed by a computer, including but not limited to magnetic storage (e.g., floppy disk, hard disk, magnetic tape, magneto-optical disk (MO), etc.), optical storage (e.g., CD, DVD, BD, HVD, etc.), and semiconductor memory (e.g., ROM, EPROM, EEPROM, non-volatile memory (NANDFLASH) 110, solid state disk (SSD)), etc.

In the solution of the present disclosure, for each pixel in the feature image, information of a pixel adjacent to the pixel in the feature image and information of a pixel non-adjacent but similar to the pixel in the feature image is applied to re-determine the pixel value of the pixel in the to-be-processed image, thereby solving problems in the prior art that the quality of the obtained image is poor due to loss of detail information caused by only using information of pixels adjacent to each pixel to denoise the image.

The above are only specific implementations of the present disclosure, but the scope of the present disclosure is not limited to this. Any transformation or replacement that those skilled in the art can understandably think of within the scope of the technology disclosed in the present disclosure should be covered by the scope of the present disclosure, and therefore, the scope of the present disclosure should be subject to the scope of the claims.

What is claimed is:

1. A medical image processing method, comprising:
   obtaining a to-be-processed image;
   performing a feature extraction on the to-be-processed image to obtain a corresponding feature image; and
   re-determining a pixel value of each pixel in the to-be-processed image based on first information and second information of a corresponding pixel in the feature image, and processing the to-be-processed image; wherein the first information is information of a pixel adjacent to the corresponding pixel in the features image, and the second information is information of a pixel that is not adjacent to and is similar to the corresponding pixel in the features image,
   wherein the re-determining a pixel value of each pixel in the to-be-processed image based on first information and second information of a corresponding pixel in the feature image, and processing the to-be-processed image comprise:
   obtaining pixels in a neighborhood with a radius r around the corresponding pixel in the feature image to form a first pixel set, and obtaining pixels similar to the corresponding pixel in the feature image and located outside the neighborhood to form a second pixel set; wherein r is a preset neighborhood radius parameter, being a positive integer;
   obtaining a first contribution rate of each first pixel in the first pixel set to the corresponding pixel in the features image, and obtaining a second contribution rate of each second pixel in the second pixel set to the corresponding pixel in the features image; wherein a sum of all the first contribution rates and all the second contribution rates is 1; and
   for each first pixel, multiplying a pixel value and the corresponding first contribution rate of the first pixel to obtain a first product; for each second pixel, multiplying a pixel value and the corresponding second contribution rate of the second pixel to obtain a second product; and adding all the first products with all the second products to obtain a sum, and taking the sum as a pixel value of the corresponding pixel in the features image.

2. The method according to claim 1, wherein the obtaining pixels similar to the corresponding pixel in the feature image and located outside the neighborhood to form a second pixel set comprises:
   calculating a Euclidean distance between a feature vector of the corresponding pixel in the feature image and a feature vector of each pixel outside the neighborhood of radius r, and obtaining N pixels with a least Euclidean distance to form the second pixel set; wherein in the second pixel set, the less the Euclidean distance, the greater the second contribution rate of the corresponding second pixel;
   N is a positive integer.

3. The method according to claim 1, further comprising:
   inputting the to-be-processed image into a preset convolutional neural network, and performing the feature extraction on the to-be-processed image through the preset convolutional neural network, to obtain the corresponding feature image and to redetermine the pixel value of each pixel in the to-be-processed image based on the first information and the second information of the corresponding each pixel in the feature image, thereby processing the to-be-processed image.

4. The method according to claim 3, further comprising: establishing the preset convolutional neural network; wherein the preset convolutional neural network comprises at least one feature extraction layer, at least one denoising layer, at least one batch of normalization layers, and at least one activation layer; each feature extraction layer is connected to one of the at least one activation layer, and each denoising layer is sequentially connected to one of the at least one batch of normalization layers and one of the at least one activation layer;

obtaining an unprocessed medical image and a corresponding processed medical image as a training data set; and training the preset convolutional neural network with the unprocessed medical image as input data and the corresponding processed medical image as a ground truth label.

5. The method according to claim 4, wherein the preset convolutional neural network further comprises at least one adaptive residual unit connected in series; each adaptive residual unit comprises three of the at least one denoising layer, three of the at least one activation layer 2, three of the at least one batch of normalization layers, and one adaptive skip connection unit.

6. The method according to claim 4, wherein the unprocessed medical image is a medical image obtained under a scanning condition less than a set time period, and the corresponding processed medical image is a medical image obtained under a scanning condition greater than the set time period.

7. The method according to claim 4, wherein the training the preset convolutional neural network with the unprocessed medical image as input data and the corresponding processed medical image as a ground truth label comprises:

training the preset convolutional neural network through a mean square error loss function; and updating a model parameter of the preset convolutional neural network through a gradient back-propagation algorithm, such that the mean square error loss function tends to be minimized.

8. A medical image processing apparatus, comprising a memory, a processor, and a computer program stored in the memory and executable by the processor; wherein the processor is capable of executing the computer program to implement:

obtaining a to-be-processed image;

performing a feature extraction on the to-be-processed image to obtain a corresponding feature image; and re-determining a pixel value of each pixel in the to-be-processed image based on first information and second information of a corresponding pixel in the feature image, and processing the to-be-processed image; wherein the first information is information of a pixel adjacent to the corresponding pixel in the features image, and the second information is information of a pixel that is not adjacent to and is similar to the corresponding pixel in the features image, wherein the re-determining a pixel value of each pixel in the to-be-processed image based on first information and second information of a corresponding pixel in the feature image, and processing the to-be-processed image comprise:

obtaining pixels in a neighborhood with a radius r around the corresponding pixel in the feature image to form a first pixel set, and obtaining pixels similar to the corresponding pixel in the feature image and located outside the neighborhood to form a second pixel set; wherein r is a preset neighborhood radius parameter, being a positive integer;

obtaining a first contribution rate of each first pixel in the first pixel set to the corresponding pixel in the features image, and obtaining a second contribution rate of each second pixel in the second pixel set to the corresponding pixel in the features image; wherein a sum of all the first contribution rates and all the second contribution rates is 1; and for each first pixel, multiplying a pixel value and the corresponding first contribution rate of the first pixel to obtain a first product; for each second pixel, multiplying a pixel value and the corresponding second contribution rate of the second pixel to obtain a second product; and adding all the first products with all the second products to obtain a sum, and taking the sum as a pixel value of the corresponding pixel in the features image.

9. The medical image processing apparatus according to claim 8, wherein the obtaining pixels similar to the corresponding pixel in the feature image and located outside the neighborhood to form a second pixel set comprises:

calculating a Euclidean distance between a feature vector of the corresponding pixel in the feature image and a feature vector of each pixel outside the neighborhood of radius r, and obtaining N pixels with a least Euclidean distance to form the second pixel set; wherein in the second pixel set, the less the Euclidean distance, the greater the second contribution rate of the corresponding second pixel;

N is a positive integer.

10. The medical image processing apparatus according to claim 8, wherein the processor is further configured to implement:

inputting the to-be-processed image into a preset convolutional neural network, and performing the feature extraction on the to-be-processed image through the preset convolutional neural network, to obtain the corresponding feature image and to redetermine the pixel value of each pixel in the to-be-processed image based on the first information and the second information of the corresponding each pixel in the feature image, thereby processing the to-be-processed image.

11. The medical image processing apparatus according to claim 10, wherein the processor is further configured to implement:

establishing the preset convolutional neural network; wherein the preset convolutional neural network comprises at least one feature extraction layer, at least one denoising layer, at least one batch of normalization layers, and at least one activation layer; each feature extraction layer is connected to one of the at least one activation layer, and each denoising layer is sequentially connected to one of the at least one batch of normalization layers and one of the at least one activation layer;

obtaining an unprocessed medical image and a corresponding processed medical image as a training data set; and training the preset convolutional neural network with the unprocessed medical image as input data and the corresponding processed medical image as a ground truth label.

12. The medical image processing apparatus according to claim 11, wherein the preset convolutional neural network further comprises at least one adaptive residual unit connected in series; each adaptive residual unit comprises three of the at least one denoising layer, three of the at least one activation layer 2, three of the at least one batch of normalization layers, and one adaptive skip connection unit.

13. The medical image processing apparatus according to claim 11, wherein the unprocessed medical image is a medical image obtained under a scanning condition less than a set time period, and the corresponding processed medical image is a medical image obtained under a scanning condition greater than the set time period.

14. The medical image processing apparatus according to claim 11, wherein the training the preset convolutional neural network with the unprocessed medical image as input data and the corresponding processed medical image as a ground truth label comprises:
  training the preset convolutional neural network through a mean square error loss function; and
  updating a model parameter of the preset convolutional neural network through a gradient back-propagation algorithm, such that the mean square error loss function tends to be minimized.

15. A non-transitory computer-readable storage medium, storing a computer program; wherein the computer program is executable by a processor to implement:
  obtaining a to-be-processed image;
  performing a feature extraction on the to-be-processed image to obtain a corresponding feature image; and
  re-determining a pixel value of each pixel in the to-be-processed image based on first information and second information of a corresponding pixel in the feature image, and processing the to-be-processed image; wherein the first information is information of a pixel adjacent to the corresponding pixel in the features image, and the second information is information of a pixel that is not adjacent to and is similar to the corresponding pixel in the features image,
  wherein the re-determining a pixel value of each pixel in the to-be-processed image based on first information and second information of a corresponding pixel in the feature image, and processing the to-be-processed image comprise:
  obtaining pixels in a neighborhood with a radius r around the corresponding pixel in the feature image to form a first pixel set, and obtaining pixels similar to the corresponding pixel in the feature image and located outside the neighborhood to form a second pixel set; wherein r is a preset neighborhood radius parameter, being a positive integer;
  obtaining a first contribution rate of each first pixel in the first pixel set to the corresponding pixel in the features image, and obtaining a second contribution rate of each second pixel in the second pixel set to the corresponding pixel in the features image; wherein a sum of all the first contribution rates and all the second contribution rates is 1; and
  for each first pixel, multiplying a pixel value and the corresponding first contribution rate of the first pixel to obtain a first product; for each second pixel, multiplying a pixel value and the corresponding second contribution rate of the second pixel to obtain a second product; and adding all the first products with all the second products to obtain a sum, and taking the sum as a pixel value of the corresponding pixel in the features image.

16. The non-transitory computer-readable storage medium according to claim 15, wherein the obtaining pixels similar to the corresponding pixel in the feature image and located outside the neighborhood to form a second pixel set comprises:
  calculating a Euclidean distance between a feature vector of the corresponding pixel in the feature image and a feature vector of each pixel outside the neighborhood of radius r, and obtaining N pixels with a least Euclidean distance to form the second pixel set; wherein in the second pixel set, the less the Euclidean distance, the greater the second contribution rate of the corresponding second pixel;
  N is a positive integer.

17. The non-transitory computer-readable storage medium according to claim 15, wherein the processor is further configured to implement:
  inputting the to-be-processed image into a preset convolutional neural network, and performing the feature extraction on the to-be-processed image through the preset convolutional neural network, to obtain the corresponding feature image and to redetermine the pixel value of each pixel in the to-be-processed image based on the first information and the second information of the corresponding each pixel in the feature image, thereby processing the to-be-processed image.

* * * * *